United States Patent [19]

Grollier et al.

[11] Patent Number: 5,180,399
[45] Date of Patent: Jan. 19, 1993

[54] PROCESS FOR DYEING KERATINOUS FIBRES WITH OXIDATION BASES COMBINED WITH AN IODIDE AND DYEING COMPOSITION EMPLOYED

[75] Inventors: Jean F. Grollier, Paris; Jean Cotteret, Verneuil-sur-Seine; Didier Garoche, Levallois-Perret, all of France

[73] Assignee: L'Oreal, Paris, France

[21] Appl. No.: 717,253

[22] Filed: Jun. 18, 1991

Related U.S. Application Data

[63] Continuation of Ser. No. 566,097, Aug. 13, 1990, abandoned, which is a continuation of Ser. No. 198,807, May 25, 1988, abandoned.

[30] Foreign Application Priority Data

May 25, 1987 [FR] France .................. 86 899

[51] Int. Cl.$^5$ ................. A61K 7/13
[52] U.S. Cl. ................. 8/405; 8/406; 8/407; 8/410; 8/423; 8/634; 424/70
[58] Field of Search ......... 8/405, 406, 407, 410, 8/423, 634; 424/70

[56] References Cited

U.S. PATENT DOCUMENTS

| | | | |
|---|---|---|---|
| 1,677,508 | 7/1928 | Winogradoff | 8/634 |
| 4,268,264 | 5/1981 | Grollier et al. | 8/412 |
| 4,321,054 | 3/1982 | Davis et al. | 8/634 |
| 4,361,421 | 11/1982 | Bugaut et al. | 8/407 |
| 4,420,637 | 12/1983 | Bugaut et al. | 8/407 |
| 4,566,875 | 11/1986 | Grollier et al. | 8/406 |
| 4,690,685 | 3/1987 | Grollier et al. | 8/407 |
| 4,804,385 | 2/1989 | Grollier et al. | 8/423 |
| 4,808,190 | 2/1989 | Grollier et al. | 8/423 |

FOREIGN PATENT DOCUMENTS 2028818 6/1970 Fed. Rep. of Germany.
53-072836 6/1978 Japan.

Primary Examiner—A. Lionel Clingman
Assistant Examiner—William S. Parks
Attorney, Agent, or Firm—Cushman, Darby & Cushman

[57] ABSTRACT

A process for dyeing keratinous fibers employs a dye composition containing an oxidation base selected from a paraphenylenediamine, an N,N'-diphenylalkylene diamine, a para-aminophenol, an ortho-aminophenol, an ortho-phenylenediamine or a heterocyclic oxidation base, in combination with iodide ions. The application of this dyeing composition to the keratinous fibers is preceded or followed by the application to the fibers of a composition containing hydrogen peroxide.

33 Claims, No Drawings

PROCESS FOR DYEING KERATINOUS FIBRES WITH OXIDATION BASES COMBINED WITH AN IODIDE AND DYEING COMPOSITION EMPLOYED

This is a continuation of application Ser. No. 07/566,097, filed Aug. 13, 1990, now abandoned, which is a continuation of application Ser. No. 07/198,807, filed May 25, 1988, now abandoned.

The present invention relates to a new process for the dyeing of keratinous fibres, especially human keratinous fibres such as hair, with oxidation bases, to the compositions employed in this process and the devices or kits containing said compositions.

For many years, either so-called "direct" dyes, capable in themselves of coloring keratinous fibres, or so-called "oxidation" dyes which, after the development of their dyeing power in an oxidizing medium, enable a coloration to be obtained which is resistant to several treatments with shampoo, to light and to inclement weather, have been used for the dyeing of keratinous fibres, and especially hair.

Oxidation dyes are generally not dyes in themselves; they are intermediate compounds initially having little or no color, commonly referred to as "oxidation bases or precursors", which develop their dyeing power in an oxidizing medium, generally consisting of hydrogen peroxide, to give rise in a basic medium to a dye in accordance with a process, either of oxidative condensation of the oxidation dye precursor with itself, or of an oxidative condensation of the "oxidation base or dye precursor" with a compound referred to as a "color modifier" or "coupler".

The variety of molecules involved, formed by these different oxidation dyes and the possibility of coupling them, makes it possible to obtain a rich palette of colorings in respect of ashen, black, natural hues and hues with glints.

A coloration of this kind is referred to as a "permanent coloration", as opposed to the coloration obtained with the so-called "direct" dyes, which is a so-called "semi-permanent" coloration.

Processes employing a pretreatment with ions in the form of soluble salts, followed by the application of oxidation dyes after an intermediate rinsing stage, have already been proposed in the past.

The applicants have discovered, and this forms the subject of the invention, a process using a composition containing, in combination oxidation bases and an iodide ion, enabling hues to be obtained which can be different or stronger than those formerly obtained with the traditional system of oxidative polymerization of these bases with couplers. They also found that the colorations thereby obtained made it possible to decrease the exposure times and, in this manner, to produce a dyeing much more rapidly than with the systems of the prior art.

This process also enables hair to be dyed with oxidation bases in an acidic medium and without employing the alkalinizing agents traditionally used in the field of oxidation dyeing, such as ammonia solution and amines, which impart an undesirable odor to the compositions employed in the process.

The colorations obtained are especially resistant to atmospheric attack and to chemical agents including, in particular, light, washing and permanent-waving.

A subject of the invention hence consists of a process for dyeing keratinous fibres employing an oxidation base and an iodide in the same composition.

Another subject of the invention consists of compositions intended for use for the dyeing of keratinous fibres, containing an oxidation base and iodide.

The subject of the invention is also multi-component dyeing kits or outfits employing the compositions used in the different stages of the dyeing process.

Other subjects of the invention will become apparent on reading the description and examples which follow.

The process for dyeing keratinous fibres, preferably human, according to the invention, is essentially characterized in that at least one composition (A) is applied on these fibres, this composition (A) containing, in a medium suitable for dyeing, at least one base chosen from para-phenylenediamines, corresponding to the formula (I):

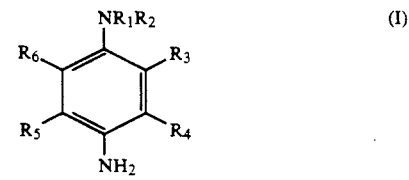

in which: $R_1$ and $R_2$, which may be identical or different, can denote hydrogen, a $C_1$–$C_6$ lower alkyl group, a $C_1$–$C_6$ alkyl radical substituted with one or more hydroxy group(s) or with a methoxy, methylsulphonylamino or aminocarbonyl group, a furfuryl group, or a phenyl radical optionally substituted with an amino group; $R_3$ and $R_6$ can denote, independently of one another, hydrogen, a $C_1$–$C_6$ lower alkoxy group, a halogen atom such as a chlorine atom, a $C_1$–$C_6$ lower alkyl group, or a $C_1$–$C_6$ lower alkyl group substituted with one or more hydroxy group(s); and $R_4$ and $R_5$ denote, independently of one another, hydrogen, a $C_1$–$C_6$ lower alkoxy group, a $C_1$–$C_6$ lower alkyl group, or a halogen atom such as chlorine, it not being possible for $R_1$ and $R_2$ simultaneously to denote hydrogen when $R_3$, $R_4$, $R_5$ and $R_6$ all denote hydrogen; as well as their salts with inorganic or organic acids, N,N'-diphenylalkylenediamines in which the phenyl groups are substituted at the para position with an OH or amino group optionally substituted with a $C_1$–$C_6$ alkyl group, it being possible for the amino groups joined by the alkylene group to be substituted with $C_1$–$C_6$ alkyl, $C_1$–$C_6$ hydroxyalkyl or $C_1$–$C_6$ aminoalkyl, para-aminophenols, ortho-aminophenols, ortho-phenylenediamines and heterocyclic oxidation bases, in combination with iodide ions, the application of this composition (A) being preceded or followed by the application of a composition (8) which contains, in a medium suitable for dyeing, hydrogen peroxide at a pH of between 2 and 12, and preferably between 2 and 7, and especially between 2 and 5.

The application of the compositions (A) and (B) is optionally separated by a rinsing.

In the process according to the invention, the iodide ion is preferably an alkali metal, alkaline earth metal or ammonium iodide, and especially potassium iodide.

Among especially preferred compounds of the formula (I), there may be mentioned 2-methyl-para-phenylenediamine, 2-methoxy-para-phenylenediamine, 2-chloro-N-methyl-para-phenylenediamine, N-furfuryl-para-phenylenediamine, 3-methoxy-N¹-methyl-paraphenylenediamine, 2-chloro-para-phenylenediamine, N-methyl-para-phenylenediamine, 2,3-dimethyl-para-phenylenediamine, 5-chloro-$N^1$-methyl-p-phenylenediamine, 5-methyl-$N^1$,$N^1$,-dimethyl-p-phenylenediamine, 5-methyl-$N^1$-ethyl-$N^1$-(aminocarbonylmethyl)-p-phenylenediamine, 5-methyl-$N^1$-ethyl-$N^1$-(methylsulphonylaminoethyl)-p-phenylenediamine, N-(2-methoxyethyl)-p-phenylenediamine, 2,6-dimethyl-p-phenylenediamine, N,N-bis(2-hydroxyethyl)-p-phenylenediamine. Among the N,N'-diphenylalkynediamines N,N'-bis-(2hydroxyethyl)-N,N'-bis(p-aminophenyl)ethylene diamine can be mentioned. There can be also employed their salts with acids such as the monohydrochlorides, dihydrochlorides or sulphates.

Among p-aminophenols which are more especially usable according to the invention, there may be mentioned p-aminophenol 2-methyl-p-aminophenol, 2,3-dimethyl-p-aminophenol, 2,6-dimethyl-p-aminophenol, 3-methoxy-p-aminophenol, 2-chloro-p-aminophenol, N-methyl-p-aminophenol and 3-(methylthio)-p-aminophenol, of which 2-methyl p-aminophenol is preferred Among ortho bases ortho-aminophenol, 5-chloro-ortho-aminophenol and ortho-phenylenediamine are chosen more especially according to the invention.

Among heterocyclic bases, it is preferable, according to the invention, to use 2,3-diamino-6-methoxypyridine and 2-(2-hydroxyethyl)amino-5-aminopyridine and their salts, and still more especially 3,6-diaminopyridine, 2,6-dimethoxy-3-aminopyridine and 2-methylamino-3-amino-6-methoxypyridine.

More especially preferred oxidation bases are 2-methyl-p-phenylenediamine, N-(2-methoxyethyl)-p-phenylenediamine, N,N-bis(2-hydroxyethyl)-p-phenylenediamine and 2-methyl-p-aminophenol.

These different oxidation bases can be used mixed or alone, in combination with iodide ions.

A subject of the invention hence consists of a process as defined above, in which the composition (A) contains exclusively an oxidation base as defined above, with iodide ions, without the presence of other compounds capable of reacting with them, for the purpose of forming a dye by coupling.

An embodiment of the invention consists in using, in combination with oxidation bases (s) 5,6-dihydroxyindole, preferably present in proportions of between 0.01 and 5% by weight, and preferably between 0.03 and 3% by weight, relative to the weight of the composition (A).

The subject of the invention is also dyeing compositions intended for use in a process for dyeing keratinous fibres, especially human hair, comprising at least one base defined above and iodide ions, in a medium suitable for dyeing. The oxidation bases used in the compositions according to the invention are preferably chosen from the preferred dyes defined above.

The composition (A), containing the oxidation base and iodide ions, generally contains the base in proportions of between 0.01 and 10% by weight relative to the total weight of the composition (A), and preferably between 0.25 and 5% by weight. The proportion of iodide in these same compositions is preferably between 0.007 and 4% by weight expressed as $I^-$ ions, and preferably between 0.08 and 1.5% by weight expresses as $I^-$ ions, relative to the total weight of the composition (A).

The hydrogen peroxide content used in the compositions (B) is generally between 1 and 40 volumes, and preferably between 2 and 20 volumes, and more especially between 3 and 10 volumes.

The ratio of the oxidation base to the odide ions is preferably between 0.05 and 10, and more especially between 0.5 and 2.

The process according to the invention is carried out by arranging exposure times, for the different compositions applied in each of the different stages of the process, of between 10 seconds and 45 minutes, and preferably of the order of 2 to 25 minutes, and more especially of the order of 2 to 10 minutes.

The applicants found, in effect, that the process according to the invention made it possible to obtain colorations that were both rapid and strong, penetrating well into the fibres, and in particular human keratinous fibres such as hair, without degrading the hair shaft. These colorations also possess good resistance to washing and to light and are odorless.

They were also able to note that hair dyed several times, following regrowth, by means of the processes and the compositions employed, according to the invention, was softer and shinier and had good mechanical properties, compared with hair dyed employing the processes and compositions of the prior art.

By means of the process and the compositions according to the invention, relatively intense colorations are obtained in relatively short times, of the order of 5 to 15 minutes.

The compositions used for carrying out the process according to the invention can be presented in various forms, such as more or less thickened or gelled liquids, creams, emulsions and foams, or other forms suitable for carrying out dyeing.

The dyeing compositions intended for use in the process according to the invention, and containing the oxidation base in combination with iodide ions, generally contain an aqueous medium consisting of water and/or a water/solvent(s) mixture, the solvent(s) preferably being chosen from organic solvents such as ethyl alcohol, propyl or isopropyl alcohol, tertbutyl alcohol, ethylene glycol, ethylene glycol monomethyl, monoethyl and monobutyl ethers, ethylene glycol monoethyl ether acetate, propylene glycol, propylene glycol monomethyl ether and dipropylene glycol monomethyl ether, and methyl lactate. The especially preferred solvents are ethyl alcohol and propylene glycol.

The oxidation bases can also be stored with the iodides in a medium consisting of anhydrous solvents, this composition being mixed at the time of use with an aqueous medium.

When the medium is aqueous, the composition (A) has a pH of between 2 and 7, and preferably between 3.5 and 7.

According to the invention, an anhydrous solvent denotes a solvent comprising less than 1% of water.

When the medium consists of a water/solvent(s) mixture, the solvents are present in concentrations preferably of between 0.5 and 75% by weight relative to the total weight of the composition, and especially between 2 and 50%, and more especially between 2 and 20%.

The compositions according to the invention can contain other adjuvants customarily used in the dyeing of keratinous fibres.

In the preferred application to the dyeing of hair, these compositions can contain, in particular, fatty amides in proportions of 0.5 to 10%, anionic, cationic, nonionic or amphoteric surfactants, or mixtures thereof, present in proportions of between 0.1 and 50% by weight, thickening agents, perfumes, sequestering agents, film-forming agents, treatment agents, dispersants, conditioners, preservatives, opacifiers, and agents that swell keratinous fibres.

The thickeners may be chosen more especially from sodium alginate, gum arabic, guar gum, biopolymers such as xanthan gum or scleroglucans, cellulose derivatives such as methylcellulose, hydroxyethylcellulose, hydroxypropylmethylcellulose, carboxymethylcellulose sodium salt and acrylic acid polymers. It is also possible to use inorganic thickening agents such as bentonite. These thickeners, used alone or mixed, are preferably present in proportions of between 0.1 and 5% by weight relative to the total weight of the composition, and advantageously between 0.5 and 3%.

The acidifying agents which are usable in the preferred embodiment of the process, employing the compositions at acid pH, may be chosen from lactic acid, acetic acid, tartaric acid, phosphoric acid, hydrochloric acid and citric acid.

It is also possible to adjust the pH with alkalinizing agents chosen, in particular, from amines such as alkanolamines and alkylamines, and alkali metal or ammonium hydroxides or cabonates, in particular when the precursors are used in the form of salts of strong acids.

When the composition is used in the form of a foam, it may be packaged under pressure in an aerosol device, in the presence of a propellant and at least one foam generator. The foam generating agents can be anionic, cationic, nonionic or amphoteric foaming polymers, or surfactants of the type defined above.

For the purpose of carrying out the process according to the invention, the different compositions may be packaged in a multi-compartment device also referred to as a kit or outfit for dyeing, comprising all the components intended for application for a single dyeing on keratinous fibres, in successive applications with or without premixing. Such devices are known per se, and can comprise a first compartment containing the composition (A), containing the oxidation base in the presence of iodide ions in a medium suitable for dyeing, and, in a second compartment, a hydrogen peroxide solution.

When the medium containing the oxidation base and the iodide ions is an anhydrous medium, it is mixed, before use, with the aqueous vehicle suitable for dyeing, optionally present in a third compartment.

The composition containing the oxidation base and iodide ions in an anhydrous medium can optionally be applied directly on wet keratinous fibres.

When the medium suitable for dyeing is aqueous, the composition in the first compartment preferably possesses a pH of between 2 and 7, and especially between 3.5 and 7. The pH of the composition containing hydrogen peroxide is between 2 and 12, but is preferably acid and between 2 and 7, and more especially between 2 and 5.

The multi-compartment devices which are usable according to the invention can be equipped with means, known per se, for mixing at the time of use, and can be packaged under an inert atmosphere.

The process and the compositions used according to the invention can be employed for dyeing hair which is natural or has already been dyed, permanent-waved or otherwise, or straightened, or hair which has been strongly or lightly bleached and optionally permanent-waved. It is also possible to use them for dyeing furs or wool.

The examples which follow are designed to illustrate the invention, without a limitation of the latter being implied.

EXAMPLE 1

The dyeing of natural, 90% white hair, was carried out by successive applications, and without rinsing between the two applications, of a dyeing solution A, of the following composition:

| | |
|---|---|
| 3-methoxy-1-N-methyl-p-phenylenediamine dihydrochloride | 1.00 g |
| potassium iodide | 0.1 g |
| ethyl alcohol | 5.00 g |
| water | qs 100 g |
| triethanolamine qs pH = 6 | |

After 5 minutes of contact, a solution B) of 12.5 volumes $H_2O_2$ (pH 3.7) was then applied for 5 minutes. The hair was rinsed with water. After drying, a bluish dark ash blond coloration was obtained.

EXAMPLE 2

Dyeing of permed, 90% white hair was carried out by successive applications, without rinsing between the two applications, of a dye A) of the following composition:

| | |
|---|---|
| 2-methyl-p-phenylenediamine dihydrochloride | 1.95 g |
| potassium iodide | 0.1 g |
| ethyl alcohol | 5.00 g |
| water | qs 100 g |
| triethanolamine qs pH = 6 | |

After 5 minutes of contact, a solution B) of 12.5 volumes $H_2O_2$ (pH 3.7) was then applied for 5 minutes. The hair was rinsed with water. After drying, a pearlescent light chestnut color was obtained.

EXAMPLE 3

Dyeing of permed, 90% white hair was carried out by successive application, and without rinsing between the two applications, of a dyeing solution A) of the following composition:

| | |
|---|---|
| N-furfuryl-p-phenylenediamine dihydrochloride | 2.6 g |
| potassium iodide | 1.00 g |
| ethyl alcohol | 5.00 g |
| water | qs 100 |
| triethanolamine qs pH = 6 | |

After 5 minutes of contact, a solution B) of 12.5 volumes $H_2O_2$ (pH 3.7) was applied for 5 minutes. The hair was rinsed with water. After drying, a slightly coppery chestnut color was obtained.

EXAMPLE 4

Example 3 was repeated using an amount of potassium iodide of 0.1 g in the dyeing solution A). A light chestnut color was obtained.

EXAMPLE 5

Dyeing of natural, 90% white hair was carried out by applying successively, and without rinsing between the two applications, a dyeing solution A) of the following composition:

| N-methyl-p-phenylenediamine | 1.95 g |
|---|---|
| potassium iodide | 0.1 g |
| ethyl alcohol | 5.00 g |
| water | qs 100 g |
| triethanolamine qs pH = 6 | |

After 5 minutes of contact, a solution of 5 volumes H$_2$O$_2$ (pH 3.9) was applied for 5 minutes. The hair was rinsed with water. After drying, a bluish medium grey color was obtained.

EXAMPLE 6

Dyeing of natural, 90% white hair was carried out by applying successively, and without rinsing between the two applications, a dyeing solution A) of the following composition:

| N-methyl-p-phenylenediamine | 1.95 g |
|---|---|
| potassium iodide | 0.1 g |
| ethyl alcohol | 5.00 g |
| water | qs 100 g |
| triethanolamine qs pH = 6 | |

After 5 minutes of contact, a solution B) of 12.5 volumes H$_2$O$_2$ (pH 3.7) was applied for 5 minutes. The hair was rinsed with water. After drying, a golden chestnut color was obtained.

EXAMPLE 7

Dyeing of natural, 90% white hair was carried out by successive applications and without rinsing between the two applications, of a dyeing solution A) of the following composition:

| N-methyl-2-chloro-p-phenylenediamine sulphate | 1.3 g |
|---|---|
| Potassium iodide | 0.1 g |
| Ethyleneglycol monobutyl ether | 20.00 g |
| Water | qs 100 g |
| Triethanolamine qs pH = 6 | |

After 5 minutes of contact, a solution B) of 12.5 volumes H$_2$O$_2$ (pH 3.7) was applied for 5 minutes. The hair was rinsed with water. After drying, a natural blond color was obtained.

EXAMPLE 8

Dyeing of permed, 90% white hair was carried out by successive applications and without rinsing between the two applications, of a dyeing solution A) of the following composition:

| 2-methoxy-p-phenylenediamine dihydrochloride | 2.11 g |
|---|---|
| Potassium iodide | 0.1 g |
| Ethyl alcohol | 5.00 g |
| Water | qs 100 |
| Triethanolamine qs pH = 6 | |

After 5 minutes of contact, a solution B) of 12.5 volumes H$_2$O$_2$ (pH 3.7) was applied for 5 minutes. The hair was rinsed with water. After drying, a dark grey coloration with glints of steel was obtained.

EXAMPLE 9

Dyeing of natural 90% white hair was carried out by successive applications, and without rinsing between the two applications, of the following dyeing composition A):

| 2-chloro-p-phenylenediamine sulphate | 2.00 g |
|---|---|
| Ammonium iodide | 1.00 g |
| Ethyl alcohol | 10.00 g |
| Xanthane gum, sold under the trade name RHODOPOL 23 SC by the company RHONE POULENC | 1.00 g |
| Glycoside alkyl ether sold at the concentration of 60% AS under the trade name TRITON CG 110 by the company SEPPIC | 5.00 g AS |
| Water | qs 100 g |
| Triethanolamine qs pH = 6.2 | |

After 5 minutes of contact, the hair was towel-dried and then a 12.5 volumes hydrogen peroxide solution (pH 3.7) was applied while massaging the scalp for 5 minutes. After rinsing the hair with water, a natural coppery chestnut color was obtained.

EXAMPLE 10

Dyeing of natural, 90% white hair was carried out by successive applications, and without rinsing between the two applications, of a solution B) of 10 volumes hydrogen peroxide which was left in contact for 5 minutes. The hair was then towel dried and the following dyeing composition A) was applied:

| N-furfuryl-p-phenylenediamine dihydrochloride | 3.00 g |
|---|---|
| Sodium iodide | 1.5 g |
| Ethyl alcohol | 10.00 g |
| Xanthane gum sold under the name RHODOPOL SC 23 by the company RHONE-POULENC | 1.00 g |
| Glycoside alkyl ether sold at the concentration of 60% AS under the trade name TRITON CG 110 by the company SEPPIC | 5.00 g AS |
| Water | qs 100 g |
| Triethanolamine qs pH = 6 | |

The scalp was massaged for 5 minutes. The hair was rinsed with water and a blond coloration with glints of grey green was obtained.

EXAMPLE 11

Dyeing of natural, 90% white hair was carried out by successive applications, and without rinsing between the two applications, of a solution B) of 5 volumes hydrogen peroxide (pH 3.9) which was left in contact for 5 minutes. The hair was then towel dried and the following dyeing composition A) was applied:

| 2-methyl-p-phenylenediamine dihydrochloride | 3.00 g |
|---|---|
| Sodium iodide | 1.00 g |
| Ethyl alcohol | 10.00 g |
| Xanthane gum sold under the trade name RHODOPOL SC 23 by the company RHONE-POULENC | 1.00 g |
| Glycoside alkyl ether sold at the concentration of 60% AS under the trade name TRITON CG 110 by the company SEPPIC | 5.00 g AS |
| Water | qs 100 |
| Triethanolamine cs pH = 6 | |

The scalp was massaged for 5 minutes. The hair was rinsed with water and a natural medium grey color was obtained.

EXAMPLE 12

Dyeing of natural, 90% white hair was carried out, by successive applications and with rinsing between the two applications, of a dyeing solution A) of the following composition:

| | |
|---|---|
| 2,3-dimethyl-p-phenylenediamine dihydrochloride | 2.1 g |
| Potassium iodide | 0.1 g |
| Ethyl alcohol | 5.00 g |
| Water | qs 100 g |
| Triethanolamine qs pH = 6 | |

After 5 minutes of contact and subsequent rinsing, an aqueous solution B) of 12.5 volumes $H_2O_2$ (pH 3.7) was applied for 5 minutes. The hair was rinsed with water. After drying, an iridescent light ash blonde color was obtained.

EXAMPLE 13

Dyeing of natural, 90% white hair was carried out by successive application of 2 compositions A) and B) with rinsing in between.

| | |
|---|---|
| Dyeing composition (A): | |
| N,N-bis(2-hydroxyethyl)-p-phenylenediamine sulphate | 1.9 g |
| Potassium iodide | 0.7 g |
| Ethyl alcohol | 5.0 g |
| Xanthane gum sold under the trade name RHODOPOL SC 23 by the company RHONE-POULENC | 2.0 g |
| Glycoside alkyl ether sold at the concentration of 60% AS under the trade name TRITON CG 110 by the company SEPPIC | 2.1 g AS |
| Triethanolamine qs pH = 6.5 | |
| Preservative | qs |
| Water | qs 100 g |
| Composition (B): | |
| Aqueous solution of 20 volumes hydrogen peroxide | 50.0 g |
| Ethyl alcohol | 5.0 g |
| Triethanolamine qs pH = 4 | |
| Water | qs 100 g |

The composition (A) was left in contact for 10 minutes. The hair was rinsed with water and then composition (B) was applied and left to act for 10 minutes. After rinsing and drying, a light brownish grey color was obtained.

EXAMPLE 14

Dyeing of natural, 90% white hair was carried out, by successive application of two compositions (A) and (B) with rinsing in between.

| | |
|---|---|
| Dyeing composition (A): | |
| 2-methyl-p-phenylenediamine dihydrochloride | 1.26 g |
| Potassium iodide | 0.7 g |
| Ethyl alcohol | 5.0 g |
| Xanthane gum sold under the trade name RHODOPOL SC 23 by the company RHONE-POULENC | 2.0 g |
| Glycoside alkyl ether sold at the concentration of 60% AS under the trade name TRITON CG 110 by the company SEPPIC | 2.1 g AS |
| Triethanolamine qs pH = 6.5 | |
| Preservative | qs |
| Water | qs 100 g |
| Composition (B): | |
| Aqueous solution of 20 volumes hydrogen peroxide | 50.0 g |
| Ethyl alcohol | 5.0 g |
| Triethanolamine qs pH = 4 | |
| Water | qs 100 g |

The composition (A) was left in contact for 10 minutes. The hair was rinsed with water and then the composition (B) was applied and left to act for 10 minutes. After rinsing and drying, a dark golden blond color was obtained.

EXAMPLE 15

Dyeing of natural, 90% white hair was carried out by successive application of two compositions (A) and (B) with rinsing in between.

| | |
|---|---|
| Dyeing composition (A): | |
| N-(2-methoxyethyl)-p-phenylenediamine dihydrochloride | 1.65 g |
| Potassium iodide | 0.7 g |
| Ethyl alcohol | 5.0 g |
| Xanthane gum sold under the trade name RHODOPOL SC 23 by the company RHONE-POULENC | 2.0 g |
| Glycoside alkyl ether sold at the concentration of 60% AS under the trade name TRITON CG 110 by the company SEPPIC | 2.1 g AS |
| Triethanolamine qs pH = 6.5 | |
| Preservative | qs |
| Water | qs 100 g |
| Composition (B): | |
| Aqueous solution of 20 volumes hydrogen peroxide | 50.0 g |
| Ethyl alcohol | 5.0 g |
| Triethanolamine qs pH = 4 | |
| Water | qs 100 g |

Composition (A) was left in contact for 10 minutes. The hair was rinsed with water and then composition (B) was applied and left to act for 10 minutes. After rinsing and drying, a medium grey-beight color was obtained.

EXAMPLE 16

Dyeing of natural, 90% white hair was carried out by successive application of two compositions (A) and (B) with rinsing in between.

| | |
|---|---|
| Dyeing composition (A): | |
| 2-methyl-p-aminophenol | 0.4 g |
| Potassium iodide | 0.35 g |
| Ethyl alcohol | 10.0 g |
| Xanthane gum sold under the trade name RHODOPOL SC 23 by the company RHONE-POULENC | 2.0 g |
| Glycoside alkyl ether sold at the concentration of 60% AS under the trade name TRITON CG 110 by the company SEPPIC | 2.1 g AS |
| Citric acid qs pH = 6.5 | |
| Preservative | qs |
| Water | qs 100 g |
| Composition (B): | |
| Aqueous solution of 20 volumes | 50.0 g |

| hydrogen peroxide | |
|---|---|
| Ethyl alcohol | 10.0 g |
| Triethanolamine qs pH = 4 | |
| Water | qs 100 g |

Composition (A) was left in contact for 10 minutes. The hair was rinsed with water and then composition (B) was applied and left to act for 10 minutes. After rinsing and drying, a beige-golden blond color was obtained.

EXAMPLE 17

Dyeing of natural, 90% white hair was carried out by successive application of two compositions (A) and (B) with rinsing in between.

| Dyeing composition (A): | |
|---|---|
| o-aminophenol | 0.35 g |
| Potassium iodide | 0.35 g |
| Ethyl alcohol | 10.0 g |
| Xanthane gum sold under the trade name RHODOPOL SC 23 by the company RHONE-POULENC | 2.0 g |
| Glycoside alkyl ether sold at the concentration of 60% AS under the trade name TRITON CG 110 by the company SEPPIC | 2.1 g AS |
| Triethanolamine qs pH = 6.5 | |
| Preservative | qs |
| Water | qs 100 g |
| Composition (B): | |
| Aqueous solution of 20 volumes hydrogen peroxide | 50.0 g |
| Ethyl alcohol | 10.0 g |
| Triethanolamine qs pH = 4 | |
| water | qs 100 g |

Composition (A) was left to act for 10 minutes. The hair was rinsed with water and then composition (B) was applied and left to act for 10 minutes. After rinsing and drying, an intense coppery-golden color was obtained.

EXAMPLE 18

Dyeing of natural permed, 90% white hair was carried out by applying in a first step the following composition:

| N,N-bis(2-hydroxyethyl)-p-phenylenediamine sulphate | 1.0 g |
|---|---|
| Potassium iodide | 1.0 g |
| Ethyl alcohol | 10.0 g |
| Xanthane gum sold under the trade name RHODOPOL SC 23 by the company RHONE-POULENC | 2.0 g |
| Glycoside alkyl ether sold under the trade name TRITON CG 110 by the company SEPPIC | 2.1 g AS |
| Triethanolamine qs pH = 6 | |
| Water | qs 100 g |

The composition was left in contact for 15 minutes. The hair was rinsed with water and then an aqueous solution of 20 volumes hydrogen peroxide was applied for 5 minutes, the pH having been adjusted to 8 with triethanolamine. After rinsing and drying, an intense golden blond was obtained on the hair.

EXAMPLE 19

| N,N-bis(2-hydroxyethyl)-p-phenylenediamine sulphate | 1.0 g |
|---|---|
| 5.6-dihydroxyindole | 0.2 g |
| Potassium iodide | 1.0 g |
| Ethyl alcohol | 10.0 g |
| Xanthane gum sold under the trade name RHODOPOL SC 23 by the company RHONE-POULENC | 2.0 g |
| Glycoside alkyl ether sold under the trade name TRITON CG 110 by the company SEPPIC | 2.1 g AS |
| Triethanolamine qs pH = 6 | |
| Water | qs 100 g |

This composition was applied for 15 minutes on natural, 90% white hair. The hair was rinsed with water and then an aqueous solution of 20 volumes hydrogen peroxide, of pH 3, was applied for 5 minutes.

After another rinse followed by drying, a slightly pearlescent medium grey was obtained.

EXAMPLE 20

Dyeing of natural permed, 90% white hair was carried out by successive application of two compositions (A) and (B).

| Dyeing composition (A): | |
|---|---|
| 3,6-diaminopyridine dihydrochloride | 1.8 g |
| Ethyl alcohol | 5.0 g |
| Potassium iodide | 1.0 g |
| Triethanolamine qs pH = 6 | |
| Preservative | qs |
| Water | qs 100 g |

Composition (A) was applied to the hair and left in contact for 5 minutes. Then, without rinsing, a composition (B) was applied: aqueous solution of 12.5 volumes hydrogen peroxide at pH 3.7, which was left to act for 5 minutes. After rinsing with water and drying, the hair was dyed a mahogany chestnut.

We claim:

1. A process for dyeing keratinous fibers comprising applying to said fibers at least one composition (A) comprising, in a medium suitable for dyeing said fibers, at least one oxidation base selected from the group consisting of (i) a paraphenylenediamine of the formula

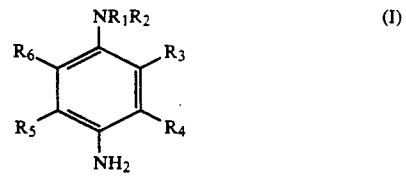

(I)

wherein $R_1$ and $R_2$, each independently, represent hydrogen, $C_1$–$C_6$ lower alkyl, $C_1$–$C_6$ alkyl substituted with at least one hydroxy or with a substituent selected from the group consisting of methoxy, methylsulphonamino radical, aminocarbonyl radical, furfuryl radical, phenyl radical and phenyl radical substituted with an amino, R$_3$ and R$_6$, each independently, represent hydrogen, C$_1$–C$_6$ lower alkoxy, halogen, C$_1$–C$_6$ lower alkyl and C$_1$–C$_6$ lower alkyl substituted with at least one hydroxy, and R$_4$ and R$_5$, each independently, represent hydrogen, C$_1$–C$_6$ lower alkoxy, C$_1$–C$_6$ lower alkyl or halogen, with the proviso that R$_1$ and R$_2$ are not simultaneously hydrogen when R$_3$, R$_4$, R$_5$ and R$_6$ all represent hydrogen, and the salts thereof with an inorganic or organic acid;

(ii) an N,N'-diphenylalkylene diamine wherein the phenyl moiety is substituted at the para position with hydroxy or amino group unsubstituted or substituted with a C$_1$–C$_6$ alkyl group, and in which the amino group joined by the alkylene is unsubstituted or substituted by a member selected from the group consisting of C$_1$–C$_6$ alkyl, C$_1$–C$_6$ hydroxyalkyl and C$_1$–C$_6$ aminoalkyl;

(iii) a para-aminophenol;

(iv) an ortho-aminophenol;

(v) an ortho-phenylenediamine; and (vi) a heterocyclic oxidation base selected from the group consisting of 2,3-diamino-6-methoxypyridine, 2-(2-hydroxyethyl)amino-5-aminopyridine, 3,6-diaminopyridine, 2,6-dimethoxy-3-aminopyridine and 2-methylamino-3-amino-6-methoxypyridine, said oxidation base being present in an amount ranging from 0.01 to 10 percent by weight based on the total weight of said composition (A), in combination with iodide ions present in an amount ranging from 0.007 to 4 percent by weight, expressed as I$^-$ ions, relative to the total weight of said composition (A), and applying to said fibers composition (B) comprising in a medium suitable for dyeing said fibers, hydrogen peroxide having a pH ranging from 2 to 12, the application of said composition (A) to said fibers, preceding or following the application of said composition (B) to said fibers.

2. The process of claim 1 wherein said composition (B) has a pH ranging from 2 to 7.

3. The process of claim 1 wherein said iodide ions are derived from an alkali metal iodide, an alkaline earth metal iodide or ammonium iodide.

4. The process of claim 1 wherein said composition (A) containing iodides in the form of alkali metal iodides, alkaline earth metal iodides or ammonium iodides and said oxidation base in a medium suitable for dyeing said fibers is applied to said fibers in a first stage and said composition (B) containing hydrogen peroxide in a medium suitable for dyeing said fibers is applied to said fibers in a second stage.

5. The process of claim 1 wherein said composition (B) comprises an aqueous solution of 1 to 40 volumes hydrogen peroxide.

6. The process of claim 1 wherein said composition (B) comprises an aqueous solution of 2 to 20 volumes hydrogen peroxide.

7. The process of claim 1 wherein each of said compositions (A) and (B) is applied to said fibers and is permitted to remain in contact therewith for a period of time ranging from 10 seconds to 45 minutes.

8. The process of claim 1 wherein each of said composition (A) and (B) is applied to said fibers and is permitted to remain in contact therewith for a period of time ranging from 2 minutes to 10 minutes.

9. The process of claim 1 wherein said paraphenylenediamine of formula I is selected from the group consisting of 2-methyl paraphenylenediamine,
2-methoxy paraphenylenediamine,
N-methyl-2-chloro paraphenylenediamine,
N-furfuryl paraphenylenediamine,
3-methoxy-N'-methyl paraphenylenediamine,
2-chloro paraphenylenediamine,
N-methyl paraphenylenediamine,
2,3-dimethylparaphenylenediamine,
5-chloro-N'-methyl paraphenylenediamine,
5-methyl-N',N'-dimethyl paraphenylenediamine,
5-methyl-N'-ethyl-N'-(aminocarbonylmethyl)paraphenylenediamine,
5-methyl-N'-ethyl-N'(methylsulphonylaminoethyl)-paraphenylenediamine,
N-(2-methoxyethyl)-paraphenylenediamine,
2,6-dimethyl paraphenylenediamine,
N,N-bis (2-hydroxyethyl) paraphenylenediamine and salts thereof with an inorganic or organic acid.

10. The process of claim 1 wherein said N,N'-diphenylalkylenediamine is N,N'-bis-(2-hydroxyethyl)-N,N'-bis-(p-aminophenyl) ethylenediamine or the salt thereof with an inorganic or organic acid.

11. The process of claim 1 wherein said paraaminophenol is selected from the group consisting of paraaminophenol,
2-methyl-paraaminophenol,
2,3-dimethyl paraaminophenol,
2,6-dimethyl paraaminophenol,
3-methoxy paraaminophenol,
2-chloro paraaminophenol,
N-methyl paraaminophenol and
3-(methylthio) paraaminophenol.

12. The process of claim 1 wherein said oxidation base is selected from the group consisting of ortho-aminophenol, 5-chloro-ortho-aminophenol and ortho-phenylenediamine.

13. The process of claim 1 wherein said composition (A) also contains 5,6-dihydroxy indole.

14. The process of claim 1 wherein said oxidation base in said composition (A) is selected from the group consisting of 2-methyl paraphenylenediamine,
N-(2-methoxyethyl) paraphenylenediamine,
N,N-bis-(2-hydroxyethyl) paraphenylenediamine and
2-methyl paraaminophenol.

15. The process of claim 1 wherein said medium suitable for dyeing said fibers in said composition (A) is an aqueous medium consisting of water or a mixture of water and a solvent, and said composition (A) has a pH ranging from 2 to 7.

16. The process of claim 15 wherein said composition (A) has a pH ranging from 3.5 to 7.

17. The process of claim 15 wherein said solvent is ethyl alcohol, propyl alcohol, isopropyl alcohol, tert. butyl alcohol, ethylene glycol, ethylene glycol monomethyl ether, ethylene glycol monoethyl ether, ethylene glycol monobutyl ether, ethylene glycol monoethyl ether acetate, propylene glycol, propylene glycol monomethyl ether, dipropylene glycol monomethyl ether or methyl lactate.

18. The process of claim 1 wherein said composition (A) is a solution wherein said medium suitable for dyeing said fibers is an anhydrous solvent.

19. The process of claim 18 wherein said anhydrous solvent is ethyl alcohol, propyl alcohol, isopropyl alcohol, tert.butyl alcohol, ethylene glycol, ethylene glycol monomethyl ether, ethylene glycol monoethyl ether, ethylene glycol monobutyl ether, ethylene glycol monoethyl ether acetate, propylene glycol, propylene glycol monoethyl ether, dipropylene glycol monomethyl ether or methyl lactate.

20. The process of claim 1 wherein one or both of said compositions (A) and (B) also includes as an adjuvant at least one of a fatty amide present in an amount ranging from 0.05 to 10 weight percent; an anionic, cationic, nonionic or amphoteric surfactant, or a mixture thereof, present in an amount ranging from 0.1 to 50 weight percent; a thickening agent selected from the group consisting of sodium alginate, gum arabic, guar gum, xanthan gum, scleroglucan, methyl cellulose, hydroxyethyl cellulose, hydroxypropylmethyl cellulose, carboxymethyl cellulose sodium salt, acrylic acid polymer, bentonite and mixtures thereof, present in an amount ranging from 0.1 to 5 weight percent; a perfume; a sequestering agent; a film-forming agent; a treatment agent; a dispersant; a preservative; an opacifier; and a keratinous fiber swelling agent.

21. A keratinous fiber dyeing composition comprising in a medium suitable for dyeing said fiber, at least one oxidation base selected from the group consisting of
(i) a paraphenylenediamine of the formula

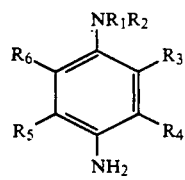

wherein
R$_1$ and R$_2$, each independently, represent hydrogen, C$_1$-C$_6$ lower alkyl, C$_1$-C$_6$ alkyl substituted with at least one hydroxy or with a substituent selected from the group consisting of methoxy, methylsulphonamino radical, aminocarbonyl radical, furfuryl radical, phenyl radical and phenyl radical substituted with an amino,
R$_3$ and R$_6$, each independently, represent hydrogen, C$_1$-C$_6$ lower alkoxy, halogen, C$_1$-C$_6$ lower alkyl and C$_1$-C$_6$ lower alkyl substituted with at least one hydroxy, and
R$_4$ and R$_5$, each independently, represent hydrogen, C$_1$-C$_6$ lower alkoxy, C$_1$-C$_6$ lower alkyl or halogen,
with the proviso that R$_1$ and R$_2$ are not simultaneously hydrogen when R$_3$, R$_4$, R$_5$ and R$_6$ all represent hydrogen,
and the salts thereof with an inorganic or organic acid;
(ii) an N,N'-diphenylalkylene diamine wherein the phenyl moiety is substituted at the para position with hydroxy or amino group unsubstituted or substituted with a C$_1$-C$_6$ alkyl group, and in which the amino group joined by the alkylene is unsubstituted or substituted by a member selected from the group consisting of C$_1$-C$_6$ alkyl, C$_1$-C$_6$ hydroxyalkyl and C$_1$-C$_6$ aminoalkyl;

(iii) a para-aminophenol;
(iv) an ortho-aminophenol;
(v) an ortho-phenylenediamine; and
(vi) a heterocyclic oxidation base selected from the group consisting of 2,3-diamino-6-methoxypyridine, 2-(2-hydroxyethyl)amino-5-aminopyridine, 3,6-diaminopyridine, 2,6-dimethoxy-3-aminopyridine and 2-methylamino-3-amino-6-methoxypyridine,
said oxidation base being present in an amount ranging from 0.01 to 10 percent by weight based on the total weight of said composition (A), in combination with iodide ions present in an amount ranging from 0.007 to 4 percent by weight, expressed as I$^-$ ions, relative to the total weight of said composition (A).

22. The dyeing composition of claim 21 which also contains 5,6-dihydroxyindole.

23. The dyeing composition of claim 21 wherein said oxidation base is present in an amount ranging from 0.25 to 5 percent by weight based on the total weight of said composition.

24. The dyeing composition of claim 21 wherein said iodide ions are present in an amount ranging from 0.08 to 1.5 percent by weight relative to the total weight of said composition.

25. The dyeing composition of claim 21 wherein the weight ratio of said oxidation base to said iodide ions ranges from 0.05 to 10.

26. The dyeing composition of claim 21 wherein the weight ratio of said oxidation base to said iodide ions ranges from 0.5 to 2.

27. A kit for dyeing keratinous fibers comprising
a first compartment containing a composition (A) comprising in a medium suitable for dyeing said fibers, at least one oxidation base selected from the group consisting of
(i) a paraphenylenediamine of the formula

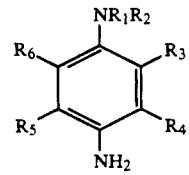

wherein
R$_1$ and R$_2$, each independently, represent hydrogen, C$_1$-C$_6$ lower alkyl, C$_1$-C$_6$ alkyl substituted with at least one hydroxy or with a substituent selected from the group consisting of methoxy, methylsulphonamino radical, aminocarbonyl radical, furfuryl radical, phenyl radical and phenyl radical substituted with an amino,
R$_3$ and R$_6$, each independently, represent hydrogen, C$_1$-C$_6$ lower alkoxy, halogen, C$_1$-C$_6$ lower alkyl and C$_1$-C$_6$ lower alkyl substituted with at least one hydroxy, and
R$_4$ and R$_5$, each independently, represent hydrogen, C$_1$-C$_6$ lower alkoxy, C$_1$-C$_6$ lower alkyl or halogen,
with the proviso that R$_1$ and R$_2$ are not simultaneously hydrogen when R$_3$, R$_4$, R$_5$ and R$_6$ all represent hydrogen,
and the salts thereof with an inorganic or organic acid;

(ii) an N,N'-diphenylalkylene diamine wherein the phenyl moiety is substituted at the para position with hydroxy or amino group unsubstituted or substituted with a $C_1$-$C_6$ alkyl group, and in which the amino group joined by the alkylene is unsubstituted or substituted by a member selected from the group consisting of $C_1$-$C_6$ alkyl, $C_1$-$C_6$ hydroxyalkyl and $C_1$-$C_6$ aminoalkyl;

(iii) a para-aminophenol;
(iv) an ortho-aminophenol;
(v) an ortho-phenylenediamine; and
(vi) a heterocyclic oxidation base selected from the group consisting of 2,3-diamino-6-methoxypyridine, 2-(2-hydroxyethyl)amino-5-aminopyridine, 3,6-diaminopyridine, 2,6-dimethoxy-3-aminopyridine and 2-methylamino-3-amino-6-methoxypyridine, said oxidation base being present in an amount ranging from 0.01 to 10 percent by weight based on the total weight of said composition (A), in combination with iodide ions present in an amount ranging from 0.007 to 4 percent by weight, expressed as $I^-$ ions, relative to the total weight of said composition (A), and a second compartment containing an aqueous composition of hydrogen peroxide.

28. The kit of claim 27 wherein the medium suitable for dyeing said fibers in said first compartment is an aqueous medium and said composition (A) has a pH ranging from 2 to 7.

29. The kit of claim 27 wherein the medium suitable for dyeing said fibers in said first compartment is an aqueous medium and said composition (A) has a pH ranging from 3.5 to 7.

30. The kit of claim 27 wherein the aqueous composition of hydrogen peroxide in said second compartment has a pH ranging from 2 to 12.

31. The kit of claim 27 wherein the aqueous composition of hydrogen peroxide in said second compartment has a pH ranging from 2 to 7.

32. A kit for dyeing keratinous fibers comprising
a first compartment containing a composition (A) comprising, in an anhydrous solvent medium, at least one oxidation base selected from the group consisting of
(i) a paraphenylenediamine of the formula

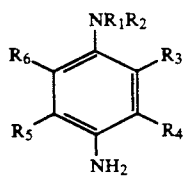

(I)

wherein $R_1$ and $R_2$, each independently, represent hydrogen, $C_1$-$C_6$ lower alkyl, $C_1$-$C_6$ alkyl substituted with at least one hydroxy or with a substituent selected from the group consisting of methoxy, methylsulphonamino radical, aminocarbonyl radical, furfuryl radical, phenyl radical and phenyl radical substituted with an amino, $R_3$ and $R_6$, each independently, represent hydrogen, $C_1$-$C_6$ lower alkoxy, halogen, $C_1$-$C_6$ lower alkyl and $C_1$-$C_6$ lower alkyl substituted with at least one hydroxy, and $R_4$ and $R_5$, each independently, represent hydrogen, $C_1$-$C_6$ lower alkoxy, $C_1$-$C_6$ lower alkyl or halogen, with the proviso that $R_1$ and $R_2$ are not simultaneously hydrogen when $R_3$, $R_4$, $R_5$ and $R_6$ all represent hydrogen, and the salts thereof with an inorganic or organic acid;

(ii) an N,N'-diphenylalkylene diamine wherein the phenyl moiety is substituted at the para position with hydroxy or amino group unsubstituted or substituted with a $C_1$-$C_6$ alkyl group, and in which the amino group joined by the alkylene is unsubstituted or substituted by a member selected from the group consisting of $C_1$-$C_6$ alkyl, $C_1$-$C_6$ hydroxyalkyl and $C_1$-$C_6$ aminoalkyl;

(iii) a para-aminophenol;
(iv) an ortho-aminophenol;
(v) an ortho-phenylenediamine; and
(vi) a heterocyclic oxidation base selected from the group consisting of 2,3-diamino-6-methoxypyridine, 2-(2-hydroxyethyl)amino-5-aminopyridine, 3,6-diaminopyridine, 2,6-dimethoxy-3-aminopyridine and 2-methylamino-3-amino-6-methoxypyridine, said oxidation base being present in an amount ranging from 0.01 to 10 percent by weight based on the total weight of said composition (A), in combination with iodide ions present in an amount ranging from 0.007 to 4 percent by weight, expressed as $I^-$ ions, relative to the total weight of said composition (A), a second compartment containing an aqueous medium suitable for dyeing said fibers for admixture with said composition (A) of said first compartment at the time of use, and a third compartment containing an aqueous composition of 1 to 40 volumes hydrogen peroxide, said composition having a pH ranging from 2 to 12.

33. The kit of claim 32 wherein said aqueous composition of hydrogen peroxide in said third compartment has a pH ranging from 2 to 7.

* * * * *